US010136908B2

(12) United States Patent
Mueller

(10) Patent No.: US 10,136,908 B2
(45) Date of Patent: *Nov. 27, 2018

(54) COAXIAL COIL LOCK

(71) Applicant: COVIDIEN LP, Mansfield, MA (US)

(72) Inventor: Peter M. Mueller, Frederick, CO (US)

(73) Assignee: COVIDIEN LP, Mansfield, MA (US)

(\*) Notice: Subject to any disclaimer, the term of this patent is extended or adjusted under 35 U.S.C. 154(b) by 0 days.

This patent is subject to a terminal disclaimer.

(21) Appl. No.: 15/644,249

(22) Filed: Jul. 7, 2017

(65) Prior Publication Data

US 2017/0303950 A1 Oct. 26, 2017

Related U.S. Application Data

(63) Continuation of application No. 15/049,367, filed on Feb. 22, 2016, now Pat. No. 9,713,479, which is a continuation of application No. 14/069,062, filed on Oct. 31, 2013, now Pat. No. 9,265,515, which is a
(Continued)

(51) Int. Cl.
| | |
|---|---|
| *A61B 17/00* | (2006.01) |
| *A61B 17/28* | (2006.01) |
| *A61B 17/29* | (2006.01) |
| *A61B 18/14* | (2006.01) |

(52) U.S. Cl.
CPC .......... *A61B 17/2833* (2013.01); *A61B 17/29* (2013.01); *A61B 18/1445* (2013.01); *A61B 2017/00309* (2013.01); *A61B 2017/00323* (2013.01); *A61B 2017/2905* (2013.01); *A61B 2017/2927* (2013.01); *A61B 2017/2929* (2013.01); *A61B 2017/2946* (2013.01)

(58) Field of Classification Search
CPC . A61B 17/28; A61B 17/29; A61B 2017/2927; A61B 2017/2929; A61B 17/2833; A61B 2017/2946
See application file for complete search history.

(56) References Cited

U.S. PATENT DOCUMENTS

| | | |
|---|---|---|
| 3,306,634 A | 2/1967 | Groves et al. |
| 3,572,325 A | 3/1971 | Bazell et al. |
| D249,549 S | 9/1978 | Pike |

(Continued)

FOREIGN PATENT DOCUMENTS

| | | |
|---|---|---|
| EP | 1201192 A1 | 5/2002 |
| EP | 1785101 A2 | 5/2007 |

(Continued)

*Primary Examiner* — Jonathan Miles

(57) ABSTRACT

A surgical instrument includes a housing and an elongated shaft extending distally therefrom. The elongated shaft includes a proximal portion, a distal portion and a flexible portion supported therebetween. The flexible portion permits pivotal movement of the distal portion of the elongated shaft and an end effector supported thereon. A locking mechanism is operatively associated with the flexible portion of the elongated shaft to selectively impede pivotal motion of the distal portion. The locking mechanism includes a locking coil disposed about an axis defined by the flexible portion of the elongated shaft. A distal end of the locking coil is coupled to the distal portion of the elongated shaft, and a proximal end of the locking coil is rotatable about the longitudinal axis to laterally approximate the locking coil to flexible portion, and thus frictionally engage the flexible portion of the elongated shaft to selectively impede articulating motion thereof.

21 Claims, 6 Drawing Sheets

Related U.S. Application Data continuation of application No. 13/186,670, filed on Jul. 20, 2011, now Pat. No. 8,574,263.

(56) References Cited

U.S. PATENT DOCUMENTS

| | | |
|---|---|---|
| D279,075 S | 6/1985 | Nuesse et al. |
| D280,378 S | 9/1985 | Nuesse et al. |
| D298,353 S | 11/1988 | Manno |
| D299,413 S | 1/1989 | DeCarolis |
| 5,174,300 A | 12/1992 | Bales et al. |
| D343,453 S | 1/1994 | Noda |
| 5,374,277 A | 12/1994 | Hassler |
| D358,887 S | 5/1995 | Feinberg |
| 5,417,203 A | 5/1995 | Tovey et al. |
| 5,476,479 A | 12/1995 | Green et al. |
| 5,483,952 A | 1/1996 | Aranyi |
| 5,501,654 A | 3/1996 | Failla et al. |
| 5,531,686 A | 7/1996 | Lundquist et al. |
| 5,601,572 A | 2/1997 | Middleman et al. |
| 5,609,601 A | 3/1997 | Kolesa et al. |
| 5,673,840 A | 10/1997 | Schulze et al. |
| 5,704,534 A | 1/1998 | Huitema et al. |
| D394,994 S | 6/1998 | Dreve |
| 5,762,067 A | 6/1998 | Dunham et al. |
| 5,779,646 A | 7/1998 | Koblish et al. |
| 5,820,009 A | 10/1998 | Melling et al. |
| 5,823,066 A | 10/1998 | Huitema et al. |
| D402,028 S | 12/1998 | Grimm et al. |
| 5,860,995 A | 1/1999 | Berkelaar |
| 5,904,667 A | 5/1999 | Falwell |
| 6,063,098 A | 5/2000 | Houser et al. |
| 6,083,234 A | 7/2000 | Nicholas et al. |
| D453,376 S | 2/2002 | McMahon et al. |
| 6,743,240 B2 | 6/2004 | Smith et al. |
| D495,413 S | 8/2004 | Perry et al. |
| D496,997 S | 10/2004 | Dycus et al. |
| D499,181 S | 11/2004 | Dycus et al. |
| 6,821,285 B2 | 11/2004 | Laufer et al. |
| 7,052,489 B2 | 5/2006 | Griego et al. |
| D524,625 S | 7/2006 | Wu |
| D527,600 S | 9/2006 | Stratford |
| D531,311 S | 10/2006 | Guerra et al. |
| D531,872 S | 11/2006 | Aglassinger |
| D533,274 S | 12/2006 | Visconti et al. |
| 7,147,650 B2 | 12/2006 | Lee |
| D541,418 S | 4/2007 | Schechter et al. |
| D541,611 S | 5/2007 | Aglassinger |
| D547,154 S | 7/2007 | Lee |
| D550,052 S | 9/2007 | Lee |
| D559,386 S | 1/2008 | Pease et al. |
| D575,401 S | 8/2008 | Hixson et al. |
| D582,038 S | 12/2008 | Swoyer et al. |
| D582,742 S | 12/2008 | Aglassinger |
| 7,533,906 B2 | 5/2009 | Luettgen et al. |
| 7,588,176 B2 | 9/2009 | Timm et al. |
| 7,588,546 B2 | 9/2009 | de Andrade |
| 7,588,575 B2 | 9/2009 | Colleran et al. |
| 7,608,081 B2 | 10/2009 | Abdelgany |
| 7,615,067 B2 | 11/2009 | Lee et al. |
| 7,618,442 B2 | 11/2009 | Spitler et al. |
| D605,488 S | 12/2009 | Aglassinger |
| D605,489 S | 12/2009 | Aglassinger |
| 7,637,410 B2 | 12/2009 | Marczyk |
| 7,670,334 B2 | 3/2010 | Hueil et al. |
| 7,789,283 B2 | 9/2010 | Shah |
| 7,819,296 B2 | 10/2010 | Hueil et al. |
| 7,819,297 B2 | 10/2010 | Doll et al. |
| 7,819,298 B2 | 10/2010 | Hall et al. |
| D627,066 S | 11/2010 | Romero |
| D628,289 S | 11/2010 | Romero |
| D628,290 S | 11/2010 | Romero |
| 7,824,411 B2 | 11/2010 | Varieur et al. |
| 7,824,413 B2 | 11/2010 | Varieur et al. |
| 7,832,612 B2 | 11/2010 | Baxter, III et al. |
| 7,837,080 B2 | 11/2010 | Schwemberger |
| 7,842,044 B2 | 11/2010 | Runco et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,887,539 B2 | 2/2011 | Dunbar, Jr. et al. |
| 7,887,541 B2 | 2/2011 | Runco et al. |
| 7,905,380 B2 | 3/2011 | Shelton, IV et al. |
| 7,905,381 B2 | 3/2011 | Baxter, III et al. |
| 7,905,907 B2 | 3/2011 | Spitler et al. |
| 7,922,061 B2 | 4/2011 | Shelton, IV et al. |
| 7,931,677 B2 | 4/2011 | Abdelgany |
| 7,934,630 B2 | 5/2011 | Shelton, IV et al. |
| 8,968,356 B2 | 3/2015 | Mueller |
| 9,084,607 B2 | 7/2015 | Mueller |
| 9,265,515 B2 | 2/2016 | Mueller |
| 9,713,479 B2 | 7/2017 | Mueller |
| 2003/0045900 A1 | 3/2003 | Hahnen et al. |
| 2005/0049614 A1 | 3/2005 | Cendan |
| 2005/0124912 A1 | 6/2005 | Griego et al. |
| 2005/0149048 A1 | 7/2005 | Leport et al. |
| 2006/0178556 A1 | 8/2006 | Hasser et al. |
| 2007/0027468 A1 | 2/2007 | Wales et al. |
| 2007/0219550 A1 | 9/2007 | Thompson et al. |
| 2007/0221701 A1 | 9/2007 | Ortiz et al. |
| 2007/0225562 A1 | 9/2007 | Spivey et al. |
| 2008/0039776 A1 | 2/2008 | Ghabrial et al. |
| 2008/0046000 A1 | 2/2008 | Lee et al. |
| 2009/0023986 A1 | 1/2009 | Stewart et al. |
| 2009/0065549 A1 | 3/2009 | Viola |
| 2009/0088792 A1 | 4/2009 | Hoell, Jr. et al. |
| 2009/0125019 A1 | 5/2009 | Douglass et al. |
| 2009/0137984 A1 | 5/2009 | Minnelli |
| 2010/0030018 A1 | 2/2010 | Fortier et al. |
| 2010/0057121 A1 | 3/2010 | Piskun et al. |
| 2010/0179540 A1 | 7/2010 | Marczyk et al. |
| 2010/0193566 A1 | 8/2010 | Scheib et al. |
| 2010/0298638 A1 | 11/2010 | Slater |
| 2010/0298854 A1 | 11/2010 | Slater |
| 2011/0184459 A1 | 7/2011 | Malkowski et al. |
| 2012/0179151 A1 | 7/2012 | Mueller |

FOREIGN PATENT DOCUMENTS

| | | |
|---|---|---|
| EP | 1842500 A2 | 10/2007 |
| JP | 2001-276091 A | 10/2001 |
| WO | 9507662 A1 | 3/1995 |
| WO | 2006/135964 A1 | 12/2006 |
| WO | 2008045348 A2 | 4/2008 |
| WO | 2008045350 A2 | 4/2008 |
| WO | 20090039510 A1 | 3/2009 |
| WO | 2011/005335 A1 | 1/2011 |

COAXIAL COIL LOCK

CROSS REFERENCE TO RELATED APPLICATIONS

The present application is a Continuation Application of U.S. patent application Ser. No. 15/049,367, filed on Feb. 22, 2016, which is a Continuation Application of U.S. patent application Ser. No. 14/069,062, filed Oct. 31, 2013, now U.S. Pat. No. 9,265,515, which is a Continuation Application of U.S. patent application Ser. No. 13/186,670, filed Jul. 20, 2011, now U.S. Pat. No. 8,574,263, the entire contents of each of which are incorporated herein by reference.

BACKGROUND

1. Technical Field

The present disclosure relates to a surgical apparatus for laparoscopic and endoscopic procedures. In particular, the disclosure relates to a surgical apparatus having a locking mechanism for maintaining a remotely-actuated component of the instrument at a particular position or orientation.

2. Background of Related Art

Typically in a laparoscopic, endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic or endoscopic surgery typically include a relatively narrow, elongated shaft extending distally from a housing, and supporting an end effector at its distal end. Arranging the shaft of such an instrument through the cannula allows a surgeon to manipulate actuators on the housing from outside the body to induce the end effector to carry out a surgical procedure at a remote internal surgical site. This type of minimally invasive procedure has proven beneficial over traditional open surgery due to reduced trauma, improved healing and other attendant advantages.

Some laparoscopic or endoscopic instruments are steerable, and thus may provide a surgeon with a range of operability suitable for a particular surgical purpose. For example, an instrument may be configured such that the end effector may be aligned with a longitudinal axis of the instrument to facilitate insertion of the elongated shaft through the cannula. Thereafter, the end effector may be induced to articulate, or move off-axis as necessary to appropriately orient the end effector for engaging the targeted tissue. Some mechanisms for articulating the distal end of an endoscopic instrument include a pair of tendons, or tension-bearing drive cables, with distal ends anchored to the articulating portion of the instrument on opposite sides of the longitudinal axis. The proximal ends of the drive cables are operatively coupled to an actuator on the housing that is responsive to manipulation by the surgeon to draw one of the drive cables proximally while simultaneously permitting distal motion in the other drive cable. This motion in the drive cables induces pivotal motion of the articulating portion of the instrument.

When the end effector of a steerable, articulating instrument has been satisfactorily positioned and oriented, a surgeon may maintain the position and orientation of the end effector by continuously exerting the necessary forces on the actuators at the housing. Alternatively, some instruments are provided with a locking mechanism that permits the surgeon to temporarily lock the position and orientation of the end effector so that a continuous exertion of force at the housing is not required. Often these locking mechanisms operate by engaging the drive cables within the housing to arrest their motion. However, regardless of the construction materials, the drive cables exhibit a spring rate that is amplified over the length of the drive cables, and thus, the drive cables may tend to stretch when external loads are applied to the elongated shaft. This tendency to stretch may be associated with an unintended change in orientation of the end effector, e.g., without a corresponding manipulation of the actuators initiated by the surgeon.

SUMMARY

The present disclosure describes a surgical instrument including a housing and an elongated shaft extending distally from the housing. The elongated shaft includes a proximal portion defining a longitudinal axis, a flexible portion including an elongated articulating support structure extending distally from the proximal portion and defining proximal and distal ends, and a distal portion supported by the distal end of the elongated articulating support structure. Bending of the articulating support structure induces pivotal movement of the distal portion of the elongated shaft with respect to the longitudinal axis. An end effector adapted for surgically treating tissue is supported by the distal portion of the elongated shaft. A locking mechanism is operable to selectively impede pivotal motion of the distal portion of the elongated shaft. The locking mechanism includes a locking coil disposed about an axis defined by the elongated support structure. The locking coil includes a distal end coupled to the distal end of the articulating support structure. A proximal end of the locking coil is rotatable about the longitudinal axis in a first direction to laterally approximate the locking coil to the elongated support structure, and in a second opposed direction to laterally separate the locking coil from the elongated support structure. An actuator is operatively coupled to the proximal end of the locking coil to impart rotational motion thereto.

The elongated support structure may include a support coil arranged as a helically coiled member including gaps between individual windings to permit bending of the support coil. The locking coil may be disposed about an exterior surface of the support coil such that rotation of the proximal end of the locking coil in the first direction effects a reduction in an inner diameter of the locking coil. The locking coil may be helically wound in a complementary direction with respect to a helical direction in which the support coil is wound. The locking coil may be constructed of a generally flat band of a pliable material. The band may exhibit a width arranged to substantially cover the gaps defined in the support coil whether the support coil is arranged in a straight configuration or an articulated configuration.

The locking coil may also be disposed within an interior lumen defined through the support coil such that rotation of the proximal end of the locking coil in the first direction effects an increase in an outer diameter of the locking coil. The locking coil may also be constructed of a round cross-section wire.

The surgical instrument may also include at least one articulation cable extending at least partially through the elongated shaft. A distal end of the articulation cable may be operatively coupled to the distal portion of the elongated shaft and a proximal end of the articulation cable may be operatively coupled an articulation actuator such that manipulation of the articulation actuator induces an attendant pivotal motion of the distal portion of the elongated shaft with respect to the longitudinal axis. The end effector may include a pair of jaw members, and at least one of the jaw members may be selectively movable between an open position substantially spaced from the other of the pair of jaw members and a closed position wherein the jaw members are closer together. At least one of the pair of jaw members may be adapted to couple to a source of electrosurgical energy.

According to another aspect of the disclosure, an articulating surgical instrument includes a housing and an elongated shaft extending distally from the housing. The elongated shaft includes a proximal portion defining a longitudinal axis, a distal portion pivotally coupled to the proximal portion, and at least one flexible portion supported between the proximal and distal portions of the elongated shaft. An end effector is supported by the distal portion of the elongated shaft, and the end effector is adapted for surgically treating tissue. At least one tensile member extends longitudinally through the elongated shaft. The at least one tensile member is selectively movable to induce an attendant bending of the flexible portion of the elongated shaft and a corresponding pivotal motion of the distal portion of the elongated shaft. A locking mechanism is operatively associated with the flexible portion of the elongated shaft to selectively vary the rigidity of the flexible portion of the elongated shaft. The locking mechanism includes an elongated helical locking coil extending along a length of the flexible portion of the elongated shaft. The locking coil includes a proximal end rotatable about the longitudinal axis and a distal end restrained from rotational motion. The locking mechanism also includes an actuator operatively coupled to the proximal end of the locking coil to impart rotational motion thereto.

The at least one tensile member may include at least one pair of articulation cables selectively movable in opposed longitudinal directions to induce the attendant pivotal motion of the distal portion of the elongated shaft. The flexible portion of the elongated shaft may include an elongated extrusion constructed of a flexible material, and the at least one pair of articulation cables may be slidably disposed within at least one pair of articulation lumens extending through the elongated extrusion.

The elongated extrusion may be arranged as a helically wound support coil including gaps between individual windings to permit bending of the support coil. The locking coil may be helically wound in an opposed direction with respect to a helical direction in which the support coil is wound. A proximal end of the support coil may include a flat face rigidly coupled to the proximal portion of the elongated shaft and a distal end of the support coil may include a flat face rigidly coupled to the distal portion of the elongated shaft. Alternatively, the support coil may include a pair of end sections that exhibit a reduced diameter with respect to a longitudinally central portion of the support coil. The end sections may be dimensioned to engage the proximal and distal portions of the elongated shaft.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
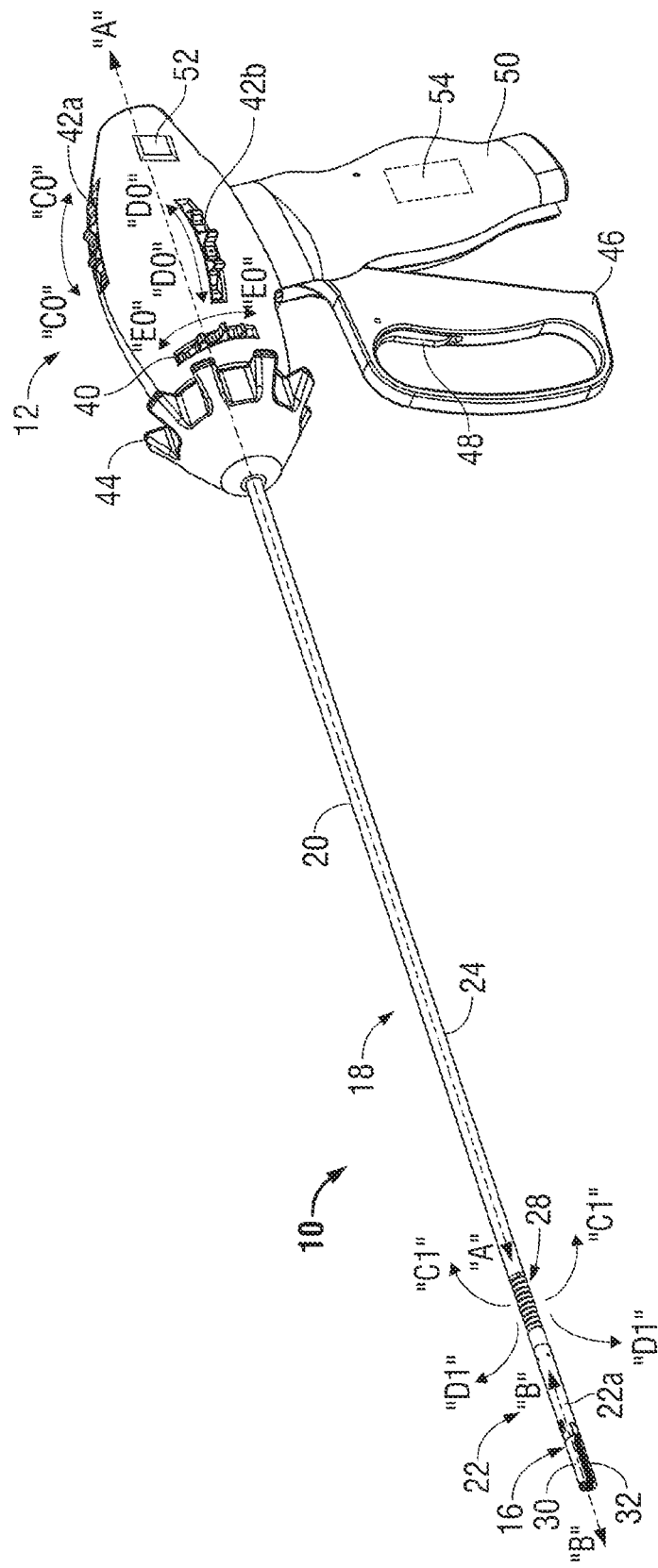
FIG. 1 is a perspective view of a surgical instrument in accordance with an embodiment of the present disclosure depicting an end effector in an aligned orientation with respect to a longitudinal axis.

Referring initially to FIG. 1, a steerable endoscopic instrument 10 is depicted in a "home" or neutral configuration. Instrument 10 includes a housing 12 near a proximal end, an end effector 16 near a distal end and an elongated shaft 18 therebetween. Elongated shaft 18 includes a proximal portion 20 extending distally from the housing 12 and an articulating distal portion 22 supporting the end effector 16. The articulating distal portion 22 includes end effector support tube 22a defining an outer surface of the distal portion 22. The proximal portion 20 defines a longitudinal axis A-A, and is sufficiently long to position the end effector 16 through a cannula (not shown) at an operative site. An outer tubular member 24 is provided over the proximal portion 20, and together with the end effector support tube 22a, provides protection and support to the interior mechanisms therein (see, e.g., FIG. 2). At least one joint or flexible portion 28 is established between the proximal and distal portions 20, 22 of the elongated shaft 18 permitting the distal portion 22 and the end effector 16 to articulate or pivot relative to the longitudinal axis A-A as described in greater detail below (see, e.g., FIG. 3). The end effector 16 defines an end effector axis B-B, which is aligned with the longitudinal axis A-A when the articulating distal portion 22 of the elongated shaft 18 is in the "home" configuration.

The end effector 16 includes a pair of opposing jaw members 30 and 32. The jaw members 30, 32 are operable from the housing 12 to move between a closed configuration and an open configuration (see FIG. 2). When the end effector 16 is in the closed configuration, a distal portion of each of the jaw members 30, 32 is adjacent the distal portion of the other of the jaw members 30, 32. The closed configuration allows the end effector 16 to assume a narrow profile to facilitate insertion of the end effector 16 through the cannula (not shown) into a body cavity. Inside the body cavity, the jaw members 30, 32 may be moved to the open configuration in which the distal portions of the jaw members 30, 32 are substantially spaced to receive tissue therebetween. The end effector 16 is configured for unilateral movement wherein only movable jaw member 32 moves relative to the end effector axis B-B (while stationary jaw member 30 remains stationary relative to the end effector axis B-B) as the end effector 16 is moved between the open and closed configurations. However, bilateral motion is also contemplated wherein both of the jaw members 30, 32 are configured to be moveable relative to the axis B-B.

Housing 12 is accessible by the surgeon from outside the body cavity to control the positioning, orientation and operation of the end effector 16 when the end effector 16 is positioned inside the body cavity at a surgical site. To provide this operability, the housing 12 supports various actuators that are operable to induce or prohibit movement in the end effector 16 through various modes. These actuators include a locking dial 40, and a pair of articulation dials 42a, 42b. The articulation dials 42a, 42b are operable to pivot the distal portion 22 of the elongated shaft 18 to various articulated orientations with respect to the longitudinal axis A-A. For example, articulation dial 42a may be rotated in the direction of arrows "C0" to induce pivotal movement in a first plane, e.g., a vertical plane, as indicated by arrows "C1." Similarly, articulation dial 42b may be rotated in the direction of arrows "D0" to induce pivotal movement in a second plane, e.g., a horizontal plane, as indicated by arrows "D1."

The locking dial 40 is operatively associated with a locking mechanism 70 (FIG. 2) to selectively adjust the rigidity of the flexible portion 28 as described below with reference to FIGS. 3 and 4. The locking dial 40 is rotatable about the longitudinal axis as indicated by arrows "E0" between locked and unlocked positions. When the locking dial 40 is in the unlocked position, e.g., rotated to the left, the flexible portion 28 is pliable, and the articulation dials 42a, 42b are functional as described above. However, when the locking dial 40 is in the locked position, e.g., rotated to the right, the flexible portion 28 is substantially more rigid, and the articulation dials 42a, 42b are inoperable to pivot the distal portion 22 of the elongated shaft 18 as described in greater detail below. Thus, the locking dial 40 is operable to lock and maintain the end effector 16 in a particular orientation with respect to the longitudinal axis A-A. As described in greater detail below, the locking dial 40 may also be movable to intermediate positions to incrementally or progressively increase and decrease resistance to articulating motion as the locking dial 40 is moved toward the locked position.

Other actuators include shoulder roll knob 44, a pivoting handle 46 and a finger trigger 48. The shoulder roll knob 44 is operable to rotate the elongated shaft 18 about the longitudinal axis A-A, and may thus cooperate with the articulation dials 42a, 42b to permit the end effector 16 to be appropriately positioned and oriented in a three dimensional environment to effectively engage tissue. The pivoting handle 46 may be approximated and separated relative to a stationary handle 50 to move the jaw members 30, 32 between the open and closed configurations. Finger trigger 48 is operable to lock the pivoting handle 46 in an approximated position with respect to the stationary handle 50, and thus maintain the jaw members 30, 32 in the closed configuration.

When the jaw members 30, 32 are in the closed configuration, the surgeon may initiate the delivery of electrosurgical energy to the jaw members 30, 32 by manipulating a push button 52 provided on the housing 12. In alternate embodiments, the delivery of electrosurgical energy may be initiated with a footswitch (not shown) or other external actuators. Push button 52 is in electrical communication with a source of electrosurgical energy such as electrosurgical generator 54. The electrosurgical generator 54 serves to produce electrosurgical energy and also to control and monitor the delivery of the electrosurgical energy. Various types of electrosurgical generators 54, such as those generators provided by Covidien—Energy-based Devices, of Boulder, Colo., may be suitable for this purpose. Electrosurgical generator 54 may be housed within the stationary handle 50 as depicted schematically in FIG. 1, or may alternatively be electrically and mechanically coupled to the instrument 10 by a cable (not shown). The electrosurgical generator 54 is in electrical communication with at least one of the jaw members 30, 32.

Figure 2:
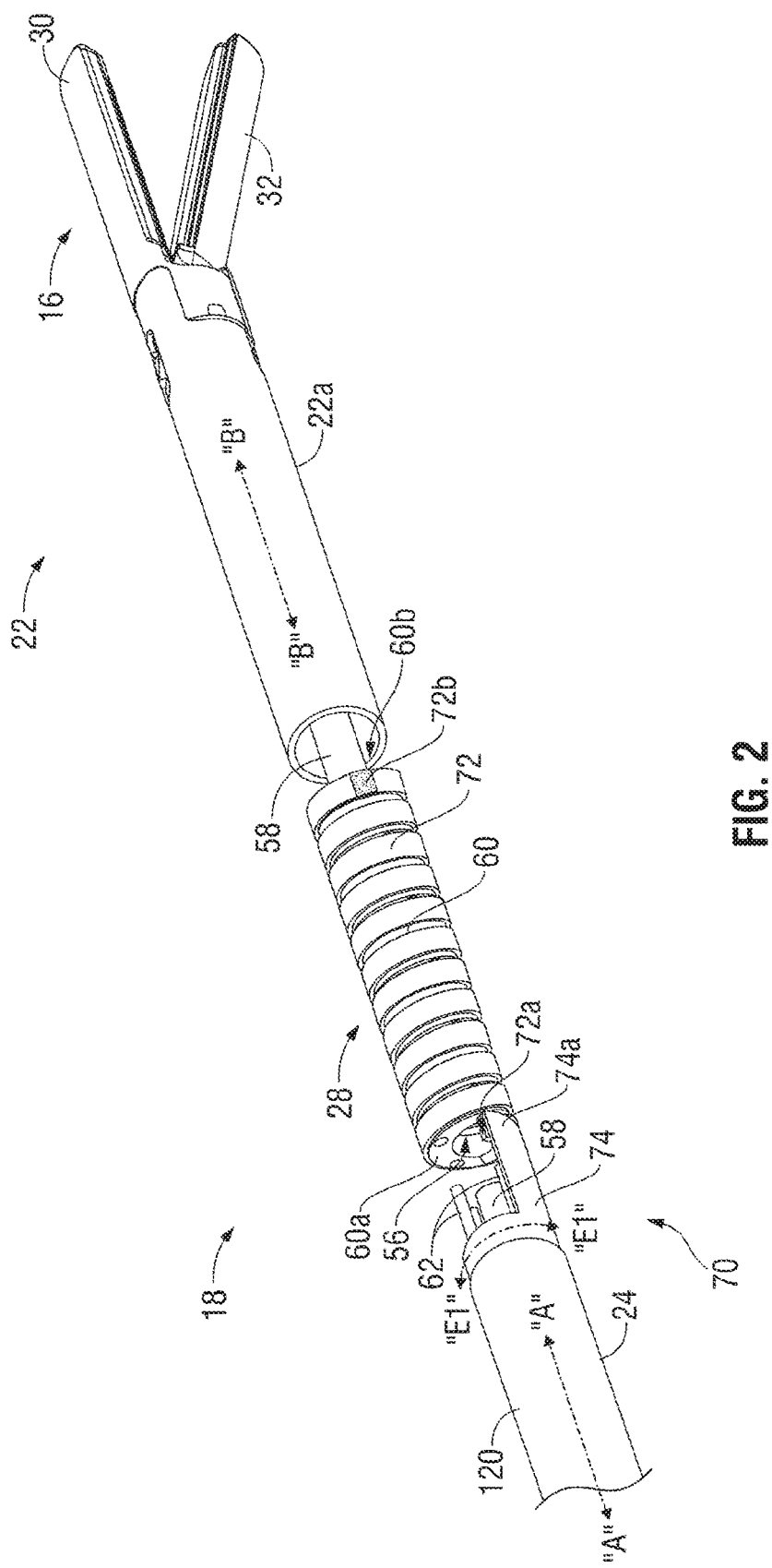
FIG. 2 is a partially exploded, perspective view of a distal end of the instrument depicting an articulating portion of the instrument arranged in a straight configuration for maintaining the end effector in the aligned orientation, and a locking mechanism operatively associated with the articulating portion to selectively permit and prohibit articulating movement of the end effector with respect to the longitudinal axis.

Referring now to FIG. 2 the distal articulating portion 22 of the elongated shaft 18 is depicted with various components separated and with the jaw members 30, 32 in an open configuration for receiving tissue therebetween. The flexible portion 28 includes a central lumen 56, which permits passage of a drive tube 58 or other implements. Other implements may include electrical cables (not shown) for supplying electrosurgical energy to the end effector 16, or a rod or catheter (not shown) for actuating a knife (not shown) arranged to transect tissue captured between the jaw members 30, 32. The drive tube 58 is operatively associated with the jaw members 30, 32 and the pivoting handle 46 (FIG. 1) such that manipulation of the pivoting handle 46 induces movement of the jaw members 30, 32 between the open and closed configurations. The drive tube 58 may be configured to transmit tensile, compressive or torsion loads to the jaw members, or alternatively, the drive tube 58 may house additional drive members (not shown) for moving the jaw members 30, 32. At least a portion of the drive tube 58 may be constructed of a conformable material to such that the drive tube 58 does not impede bending of the flexible portion 28 of the elongated shaft 18.

An articulating structural support such as support coil 60 provides structural support to the flexible portion 28 of the elongated shaft 18. A proximal end 60a and a distal end 60b of the support coil 60 include flat mating surfaces 60c (see FIG. 3) to facilitate the connection of the support coil 60 to the proximal portion 20 of the elongated shaft 18 and the end effector support tube 22a respectively. The support coil 60 is arranged as a single, helically coiled, elongated member, and is constructed of a pliable material such as stainless steel, titanium or a medical-grade plastic. This arrangement permits elastic bending of the flexible portion 28 to pivot the distal portion 22 of the elongated shaft 18 relative to the longitudinal axis A-A. In other embodiments, (not shown) the articulating structural support may be constructed as a flexible, continuous cylindrical extrusion, or as a cylindrical extrusion with non-helical patterns cut into to provide appropriate bending properties to the articulating structural support. In still other alternate embodiments, the articulating structural support may be constructed as a plurality of discrete rigid segments that are pivotally arranged with respect to one another to permit the distal portion 22 to pivot relative to the longitudinal axis A-A.

The support coil 60 permits passage of four tensile members, such as articulation cables 62. A distal end of each of the articulation cables 62 is secured to the distal end 60b of the support coil 60 (see FIG. 3). In other alternative embodiments, (not shown) the distal ends of the articulation cables 62 may be secured to a component of the distal articulating portion 22, e.g., the end effector support tube 22a. A proximal end (not shown) of each articulation cable 62 is operatively associated with one of the articulation dials 42*a*, 42*b* (FIG. 1). The articulation dials 42*a*, 42*b* are each operable impart opposed longitudinal motion (see FIG. 3) to a respective pair the articulation cables 62, and thus pivotal motion of the distal portion 22 about the longitudinal axis A-A. The articulation cables 62 are arranged near an outer circumference of the support coil 60 and exhibit a radial spacing of about 90 degrees. Thus, the articulation cables 62 define two orthogonal planes of articulation in which the distal portion 22 of the elongated shaft 18 may pivot.

The articulation cables 62 may be constructed of stainless steel wire or other material suitable for transmitting tensile forces to the distal end 60*b* of the support coil 60. Regardless of the construction materials, the articulation cables 62 exhibit a spring rate that is amplified over the length of the articulation cables 62, and thus, the articulation cables 62 may tend to stretch when external loads are applied to the elongated shaft 18. This tendency to stretch may be associated with an unintended change in orientation of the distal portion 22 of the elongated shaft 18, e.g., without a corresponding movement of the articulation dials 42*a*, 42*b* (FIG. 1) initiated by the surgeon. To diminish this unintended movement of the articulation cables 62 and end effector 16, a locking mechanism 70 that permits the flexible portion 28 to exhibit a variable rigidity without directly engaging the articulation cables 62.

The locking mechanism 70 includes a locking coil 72 coaxially coiled around the support coil 60. The locking coil 72 is constructed of a flat band of stainless steel wound to have an inside diameter slightly larger than an outside diameter of the support coil 60. This arrangement establishes a sliding fit between the locking coil 72 and the support coil 60. The locking coil 72 may alternatively be manufactured by machining a helical cut into a continuous tube stock, or the locking coil 72 may be manufactured by rigidly coupling a plurality of discrete components (not shown) to one another.

A proximal section 72*a* of the locking coil 72 is welded or otherwise fixedly coupled to a distal end of a drive tube 74, and a distal section 72*b* of the locking coil corresponding section of the support coil 60, and a proximal section 72*b* of the locking coil 72 is welded or otherwise fixedly coupled to the distal end 60*b* of the support coil 60. A proximal end (not shown) of the drive tube 74 is operatively associated with the locking dial 40 (FIG. 1) such that rotation of the locking dial 40 in the direction of arrows "E0" (FIG. 1) induces a corresponding rotation of the drive tube 74 in the direction of arrows "E1" about the longitudinal axis A-A. As described in greater detail below with reference to FIGS. 3 and 4, rotation of the drive tube 74 in the direction of arrows "E1" twists the locking coil 72 to effect a change in the frictional contact between an inner surface of the locking coil 72 and an outer surface of the support coil 60, and thus a changes the bending resistance exhibited by the support coil 60.

Figure 3:
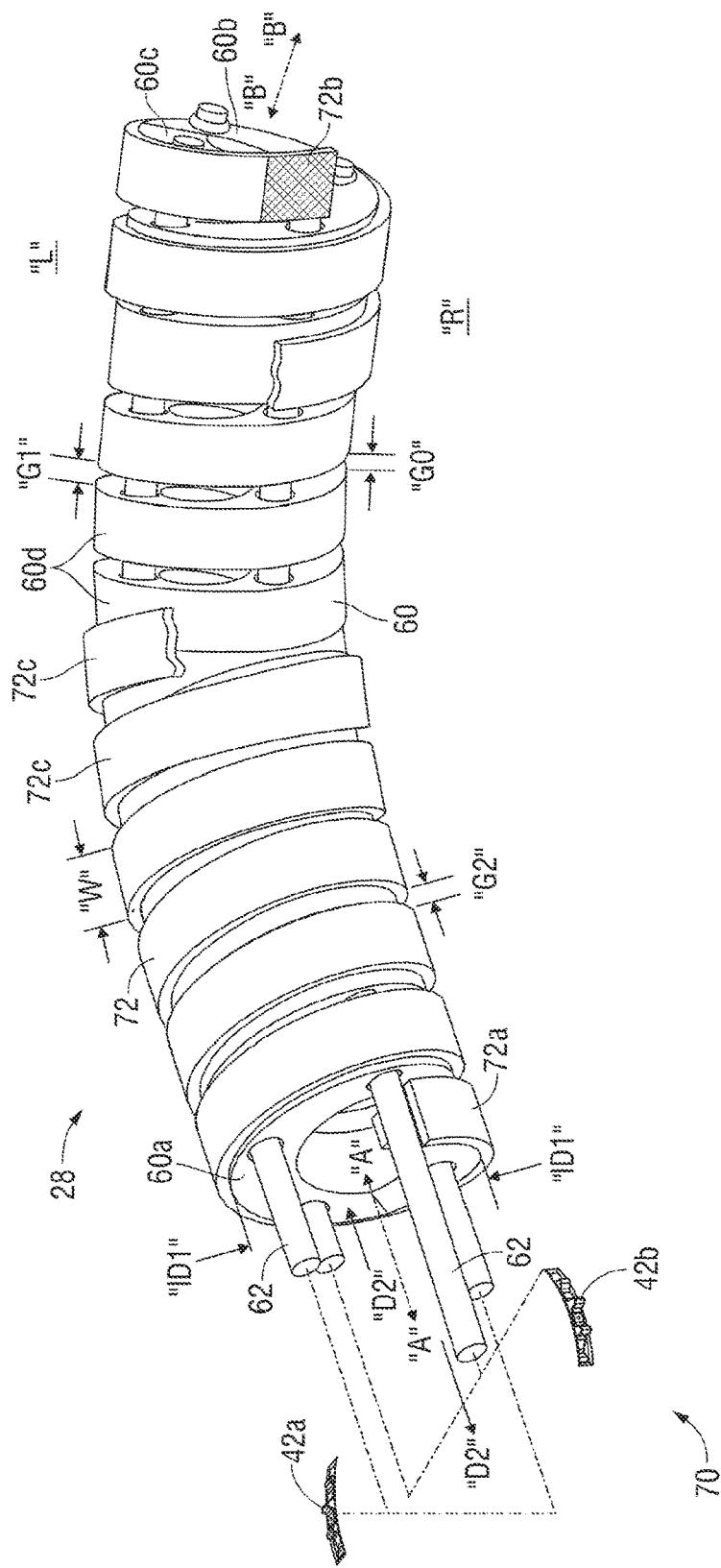
FIG. 3 is a perspective view of the articulating portion of the instrument in a curved configuration with the locking mechanism in an unlocked configuration.

Referring now to FIG. 3, the locking mechanism 70 is depicted in an unlocked configuration that permits the flexible portion 28 to be moved to a curved or articulated configuration. Movement of the flexible portion 28 to the articulated configuration allows the end effector axis B-B to be obliquely arranged with respect to the longitudinal axis A-A, and thus the permits the end effector 16 (FIG. 2) to be appropriately positioned and oriented relative to targeted tissue (not shown). The jaw members 30, 32 may be moved to the open configuration to receive the tissue by manipulating pivoting handle 46 (FIG. 1) to move the drive tube 60.

To move the flexible portion 28 from the straight configuration of FIG. 2 to the curved configuration of FIG. 3, the surgeon may manipulate the articulation dials 42*a*, 42*b* to the draw particular articulation cables 62 proximally while opposed articulation cables 62 are advanced distally. For example, manipulation of articulation dial 42*b* induces opposed movement of the articulation cables 62 as indicated by arrows "D2." An articulation cable 62 on a right side "R" is drawn proximally to induce an approximation of the individual windings 60*d* of the support coil 60 on the right side "R." Each winding 60*d* becomes separated from neighboring windings 60*d* by a reduced gap distance "G0" on the right side "R". On the left side "L," the opposing articulation cable 62 is permitted to translate distally such that the windings 60*d* separate to an increased gap distance "G1." The flexible portion 28 thus bends in a horizontal plane of articulation to the right. Similarly, manipulation of the articulation dial 42*a* induces opposed longitudinal motion in the articulation cables 62 to induce the flexible portion 28 to bend in a vertical plane of articulation. In this manner, the surgeon may manipulate articulation dials 42*a*, 42*b* in combination to achieve any three-dimensional angle of the end effector axis B-B with respect to the longitudinal axis A-A.

Since a sliding fit is established between the support and locking coils 60, 72 when the locking mechanism 70 is in the unlocked configuration, the locking coil 72 does not impede the bending of the support coil 60. The locking coil 72 is positioned about the support coil 60 to cover the gaps between the individual windings 60*d* of the support coil 60, whether the flexible portion 28 is in the straight configuration (FIG. 2) or the curved configuration (FIG. 3). The pitch, the gap distance "G2" between individual windings 72*c*, and/or a width "W" of the individual windings 72*b* of the locking coil 72, however, may be varied such that the gaps between the windings 60*d* of the support coil 60 remain uncovered if desired.

Figure 4:
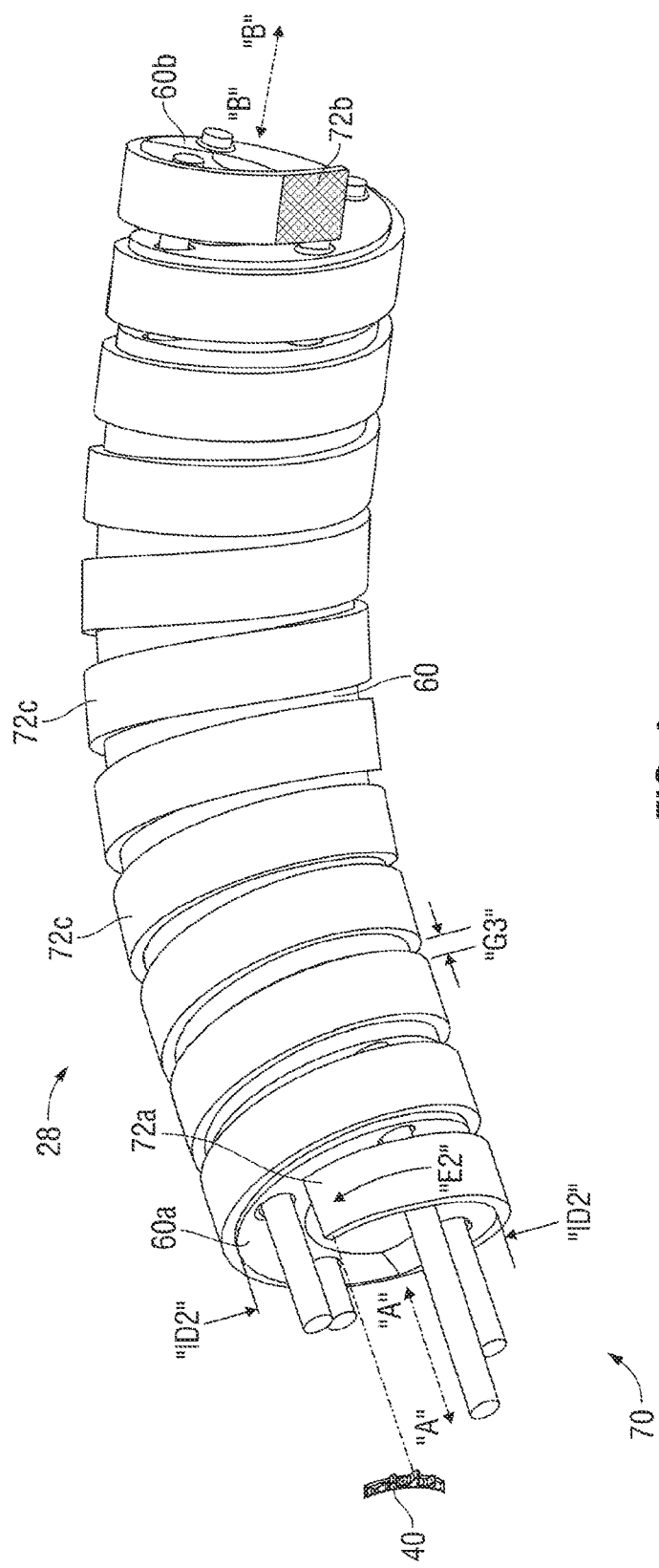
FIG. 4 is a perspective view of the articulating portion of the instrument in a curved configuration with the locking mechanism in a locked configuration.

Referring now to FIG. 4, the locking mechanism 70 is moved to a locked configuration that maintains the flexible portion 28 in the curved or articulated configuration. The locking mechanism 70 may similarly be moved to the locked configuration to maintain the flexible portion 28 in the straight configuration of FIG. 2. To move the locking mechanism 70 to the locked configuration, the surgeon manipulates the locking dial 40 to rotate drive tube 74 (FIG. 2), and thus the proximal end 72*a* of the locking coil 72 about the longitudinal axis A-A in the direction of arrow "E2." Since the distal end 72*b* of the locking coil 72 is fixedly welded to the distal end 60*b* of the support coil 60, the distal end 72*b* of the locking coil 72 remains stationary while the proximal end 72*a* rotates. The resulting relative motion of the proximal end 72*a* with respect to the distal end 72*b* decreases the gap distance between the individual windings 72*c* of the locking coil 72 to a reduced gap distance "G2." Correspondingly, the pitch of the locking coil 72 increases, i.e., the number of individual windings 72*c* per unit length, while the inside diameter of the locking coil 72 decreases to a reduced diameter "ID2."

The reduction of the inner diameter to "ID2" laterally approximates the locking coil 72 to the support coil 60, and thus binds the locking coil 72 to the support coil 60 as a friction fit is established. A greater degree of friction develops between the support and locking coils 60, 72 with increasing torque supplied to the proximal end 72*a* of the locking coil 72, and thus, the locking coil 72 provides a variable resistance to bending of the support coil 60. The support and locking coils 60, 72 may be manufactured with textured surfaces adapted to enhance the binding friction developed therebetween. Alternatively or additionally, the support and locking coils 60, 72 may be constructed of materials of dissimilar hardness such that the locking coil 72 induces compressive deformation of the support coil 60 to enhance the friction generated. When a sufficient torque is applied, the support coil 60, and thus, the flexible portion 28 of the elongated shaft 18 is locked in the particular articulated configuration achieved by movement of the articulation cables 62.

By locking the configuration of the flexible portion 28, the surgeon provides a stable platform for end effector 16 (FIG. 1) to be moved to the closed configuration about tissue. The jaw members 30, 32 are permitted to clamp the tissue with an appropriate closure force, and electrosurgical energy may be provided to treat the tissue without unintended motion of the end effector 16. Since the articulation cables 62 need not be engaged to maintain the articulated position of the distal portion 22, any movement or stretching of the articulation cables 62 will not be transmitted to the end effector 16.

When the surgical procedure is complete, the surgeon may return the locking dial 40 to the unlocked position to release the binding friction of the locking coil 72 from the support coil 60. The proximal portion 72a of the locking coil 72 is moved in the direction opposite arrow "E2" effecting a reduction in pitch and corresponding increase in the inside diameter of the locking coil 72. The flexible portion 28 of the elongated shaft 18 is thus returned to a pliable condition in which the surgeon may once again manipulate the articulation dials 42a, 42b to return the articulating distal portion 22 of the elongated shaft 18 to the aligned configuration depicted in FIG. 1. The aligned configuration facilitates withdrawal of the end effector 16 from the operative site through a cannula (not shown).

Figure 5:
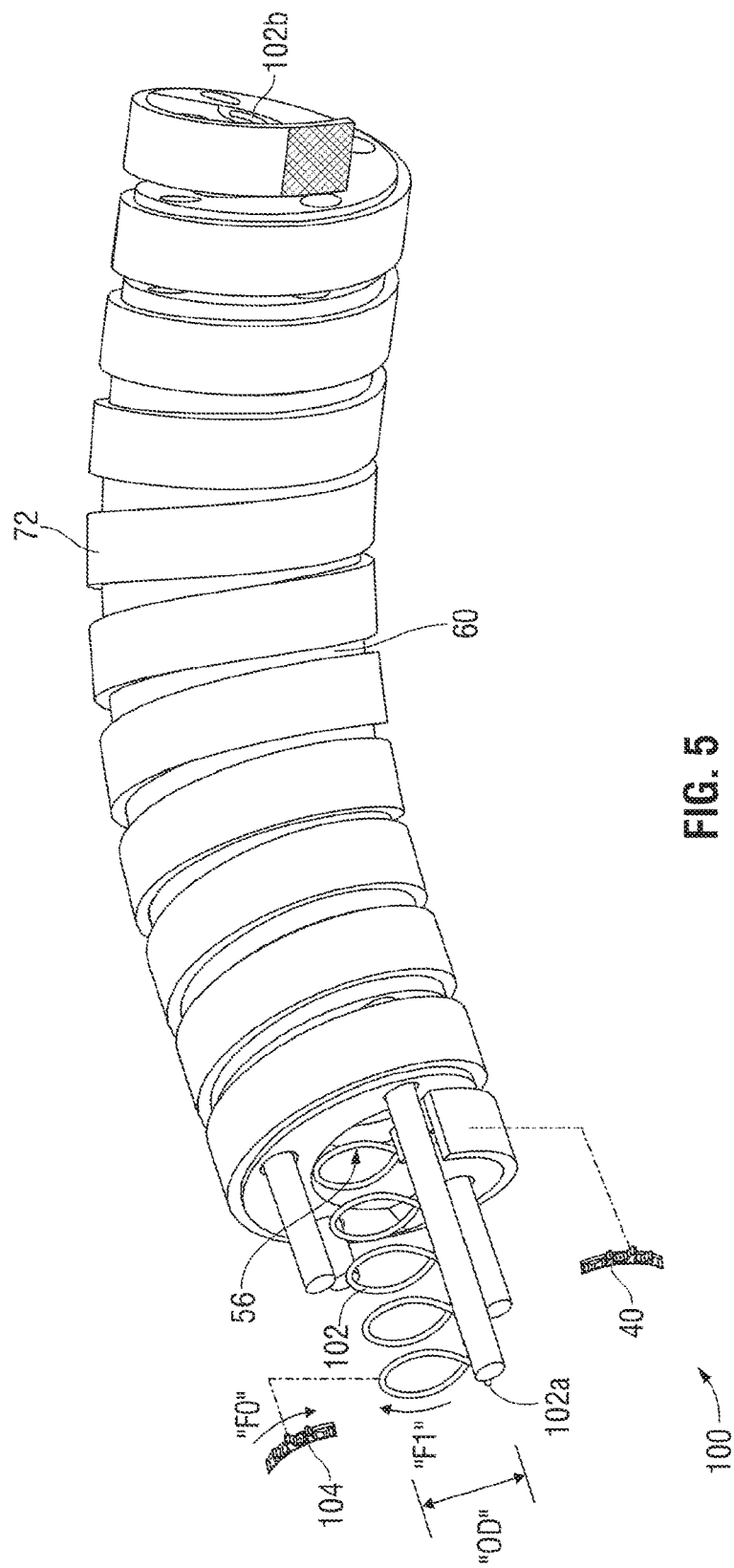
FIG. 5 is a perspective view of an alternate embodiment of an articulating portion of the surgical instrument depicting locking coils disposed against inner and outer surfaces of an articulating coil.

Referring now to FIG. 5, an alternate embodiment of a locking mechanism 100 includes a pair of locking coils 72, 102. The locking coil 72 is arranged about the outer surface of the support coil 60, and operates as described above with reference to FIGS. 4 and 5. The locking coil 102 may be provided to supplement the binding friction generated by the locking coil 72, or in alternative embodiments (not shown) the locking coil 102 may be employed exclusively to selectively lock the configuration of the support coil 60.

The locking coil 102 is constructed of as a round cross-section wire, and is arranged to extend through the central lumen 56 defined in the support coil 60. A proximal end 102a of the locking coil 102 is operatively associated with an actuator such as locking dial 104, and a distal end 102b of the locking coil 102 is welded or otherwise fixedly coupled to an interior wall of the central lumen 56. The locking coil 60 is wound to have an outer diameter "OD" slightly smaller than an inside diameter of the central lumen 56 of support coil 60. This arrangement establishes a sliding fit between the locking coil 102 and the support coil 60. The coil 102 occupies only an outer periphery of the central lumen 56, and thus, the central lumen 56 may still provide passage of drive tube 58 (FIG. 2), or other implements.

The operation of the locking coil 102 is similar to the operation of the locking coil 72. A surgeon may manipulate the locking dial 104 in the direction of arrow "F0" to induce rotation of the proximal end 102a of the locking coil 102 in the direction of arrow "F1." Since the position of the distal end 102b of locking coil 102 is fixed with respect to the support coil 60, the rotation of the proximal end 102a effects an increase in the outer diameter "OD" of the locking coil 102. This increase in the outer diameter "OD" generates a binding friction lock between the locking coil 102 and the interior surface of the central lumen 56.

In other embodiments (not shown) a helical groove may be manufactured into the inner surface of the central lumen 56 to receive the locking coil 102. When the locking coil 102 is received in a helical groove, the central lumen 56 is free from obstructions such that the drive tube 58 (FIG. 2) or other implements may pass unencumbered therethrough. A helical groove also provides a greater surface area for generating the binding friction between the support coil 60 and the locking coil 102. The helical groove and locking coil 102 may also effectively form an interfering thread lock where the groove is manufactured to exhibit a dissimilar pitch with respect to the locking coil 102. An interfering thread lock could also be generated by providing a helical groove on the outer surface of the support coil 60 for receiving the locking coil 72.

Figure 6:
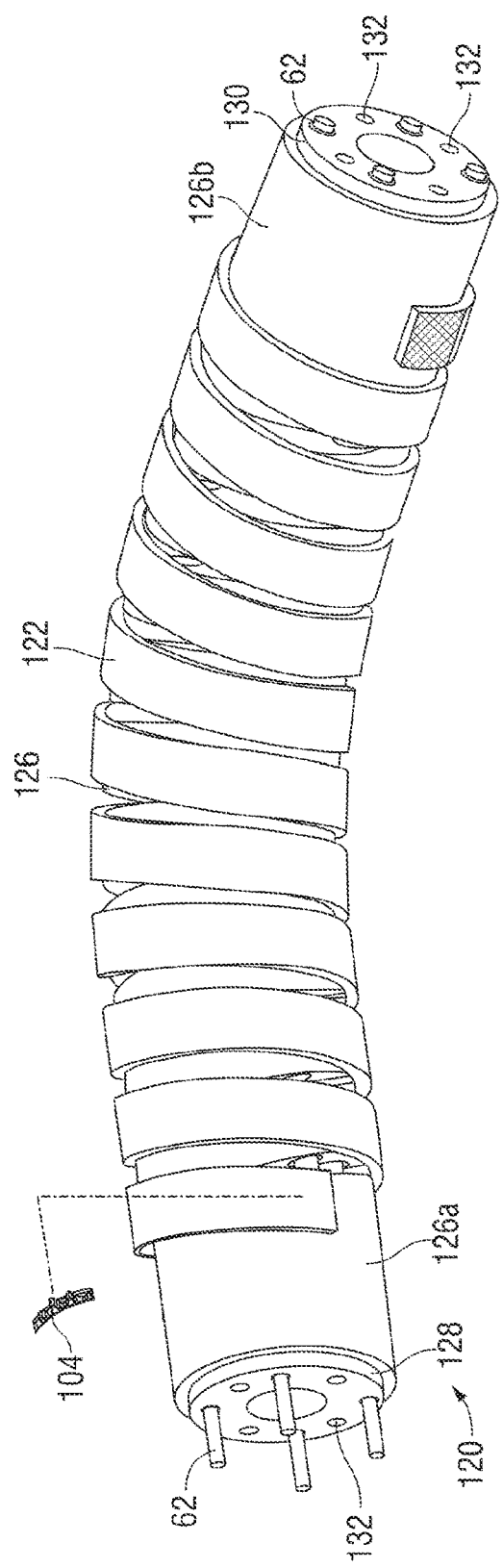
FIG. 6 is a perspective view of an additional alternate embodiment of an articulating portion of the surgical instrument depicting an outer locking coil wound in an opposite direction with respect to the articulating coil.

Referring now to FIG. 6, another alternate embodiment of a locking mechanism 120 includes a locking coil 122 coiled about a support coil 126. The locking coil 122 is wound in an opposite helical direction than the direction in which the support coil 126 is wound. The locking coil 122 is operatively coupled to the locking dial 104, and operates in the manner of locking coil 72 described above with reference to FIGS. 3 and 4, i.e., the locking dial 104 is operable to increase and decrease the frictional resistance between the locking coil 122 and the support coil 126.

The support coil 126 includes a proximal end 126a and a distal end 126b protruding from the longitudinal ends of the locking coil 122. The protruding proximal and distal ends 126a, 126b each include a respective reduced diameter portion 128, 130 dimensioned to facilitate connection with structural tubular members, e.g., outer tubular member 24 and/or end effector support tube 22a. In other embodiments (not shown), a support coil may be manufactured monolithically with the outer tubular member 24 and/or end effector support tube 22a. The support coil 126 also includes a set of four lumens 132 radially interspaced between the articulation cables 62. The lumens 132 permit passage of implements such as electrical cables (not shown) for supplying electrosurgical energy to the end effector 16 or additional control mechanism.

Although the foregoing disclosure has been described in some detail by way of illustration and example, for purposes of clarity or understanding, it will be obvious that certain changes and modifications may be practiced within the scope of the appended claims.

What is claimed is:
1. A surgical instrument, comprising:
    a housing;
    an elongated shaft extending distally from the housing and defining a longitudinal axis, the elongated shaft including a flexible portion configured to movably support an end effector such that, bending of the flexible portion is configured to induce pivotal movement of the end effector with respect to the longitudinal axis; and
    a locking mechanism coaxially disposed about the flexible portion and selectively rotatable relative to the flexible portion about the longitudinal axis, wherein upon rotation of the locking mechanism about the longitudinal axis in a first direction, the locking mechanism is configured to laterally engage the flexible portion to impede bending of the flexible portion and pivotal movement of the end effector, and wherein upon rotation of the locking mechanism about the longitudinal axis in a second direction, the locking mechanism is configured to laterally disengage from the flexible portion enabling flexure of the flexible portion and pivotal movement of the end effector.

2. The surgical instrument according to claim 1, wherein upon flexure of the flexible portion, the locking mechanism is rotatable in the first direction to lock the flexible portion in a bent configuration.

3. The surgical instrument according to claim 1, wherein the flexible portion includes a support coil and the locking mechanism includes a first locking coil disposed about the support coil.

4. The surgical instrument according to claim 3, wherein the first locking coil includes a first section coupled to the support coil and a second section rotatable about the longitudinal axis to rotate the first locking coil relative to the support coil.

5. The surgical instrument according to claim 4, wherein the first locking coil is coiled around an outer surface of the support coil such that the support coil is slidably disposed within the first locking coil and rotation of the second section of the first locking coil in the first direction decreases an inner diameter of the first locking coil such that the first locking coil frictionally engages the outer surface of the support coil.

6. The surgical instrument according to claim 5, wherein the locking mechanism further includes a second locking coil disposed within a central lumen defined by the support coil, wherein the second locking coil includes a first section coupled to the support coil and a second section rotatable about the longitudinal axis to rotate the second locking coil relative to the support coil.

7. The surgical instrument according to claim 6, wherein the second locking coil is disposed about an inner surface of the support coil such that rotation of the second section of the second locking coil in the first direction increases an outer diameter of the second locking coil such that the second locking coil frictionally engages the inner surface of the support coil.

8. The surgical instrument according to claim 6, wherein the second locking coil is constructed from a wire having a round cross-section.

9. The surgical instrument according to claim 6, wherein the first and second locking coils are helically wound in a complementary direction with respect to a wound direction of the support coil.

10. The surgical instrument according to claim 6, wherein the support coil includes a first helical groove defined on an outer surface thereof and a second helical groove defined on the inner surface thereof, wherein the first helical groove is configured to receive the first locking coil and the second helical groove is configured to receive the second locking coil.

11. The surgical instrument according to claim 3, wherein the support coil includes a gap defined between each individual winding of the support coil to facilitate flexure of the support coil relative to the longitudinal axis.

12. The surgical instrument according to claim 11, wherein the first locking coil is constructed of a generally flat band of a pliable material.

13. The surgical instrument according to claim 12, wherein the generally flat band of the pliable material includes an adjustable width arranged to substantially cover the gap defined between each individual winding of the support coil either in a straight configuration or an articulated configuration.

14. An articulating surgical instrument, comprising:
a housing;
an elongated shaft extending distally from the housing and defining a longitudinal axis and including a flexible portion including at least one helical groove defined therein having a helical pitch; and
at least one locking coil extending along the flexible portion and having a coil pitch dissimilar from the helical pitch of the helical groove, the at least one locking coil selectively transitionable to be received within the at least one helical groove of the flexible portion, wherein engagement between the coil pitch and the helical pitch is configured to provide an interfering thread lock between the flexible portion and the at least one locking coil.

15. The articulating surgical instrument according to claim 14, wherein the at least one locking coil includes a distal section restrained from rotational motion and a proximal section rotatable about the longitudinal axis to selectively vary the rigidity of the flexible portion of the elongated shaft.

16. The articulating surgical instrument according to claim 14, wherein the at least one helical groove of the flexible portion includes a first helical groove defined on an outer surface thereof and a second helical groove defined on an inner surface thereof.

17. The articulating surgical instrument according to claim 16, wherein the at least one locking coil includes a first locking coil disposed adjacent the first helical groove and a second locking coil disposed adjacent the second helical groove, wherein the first locking coil and the second locking coil are selectively transitionable to be received within the first helical groove and the second helical groove, respectively.

18. The articulating surgical instrument according to claim 14, further including a tensile member extending longitudinally through the elongated shaft, the tensile member selectively movable to articulate the flexible portion of the elongated shaft.

19. The articulating surgical instrument according to claim 18, wherein the tensile member includes at least one articulation cable selectively movable in opposite longitudinal directions to articulate the flexible portion of the elongated shaft.

20. The articulating surgical instrument according to claim 14, further including an end effector having a pair of jaw members supported by a distal portion of the elongated shaft, wherein at least one of the pair of jaw members is selectively movable between an open position wherein the jaw members are spaced apart and configured to receive tissue and a closed position wherein the jaw members are approximated.

21. The articulating surgical instrument according to claim 20, wherein at least one of the pair of jaw members is adapted to couple to a source of electrosurgical energy.

* * * * *